United States Patent [19]

Boger

[11] Patent Number: 4,668,663

[45] Date of Patent: May 26, 1987

[54] RENIN INHIBITORS CONTAINING HOMOPHE[8]

[75] Inventor: Joshua S. Boger, Bryn Mawr, Pa.

[73] Assignee: Merck & Co., Inc., Rahway, N.J.

[21] Appl. No.: 593,756

[22] Filed: Mar. 27, 1984

[51] Int. Cl.[4] .................... A61K 37/43; C07K 7/06
[52] U.S. Cl. ................................... 514/15; 514/16;
514/17; 530/327; 530/328; 530/329
[58] Field of Search .............. 260/112.5 R; 514/15,
514/16, 17; 530/327, 328, 329

[56] References Cited

U.S. PATENT DOCUMENTS

| | | | |
|---|---|---|---|
| 4,218,474 | 8/1980 | Barnish et al. | 260/112.5 R |
| 4,384,994 | 5/1983 | Veber et al. | 260/112.5 R |
| 4,397,786 | 8/1983 | Evans et al. | 260/404 |
| 4,470,971 | 9/1984 | Boger et al. | 260/112.5 R |
| 4,478,826 | 10/1984 | Veber et al. | 260/112.5 R |
| 4,479,941 | 10/1984 | Veber et al. | 260/112.5 R |
| 4,485,099 | 11/1984 | Boger et al. | 260/112.5 R |

OTHER PUBLICATIONS

Trends in Biochem. Sci., 1:205–208 (1976), Tang et al.
J. Biol. Chem., 251, 7088–7094, 1976.
Nature, 303, 81–84 (1983) Boger et al.
Federation Proc. 35, 2494–2501, 1976; Marshall.
Proc. Natl. Acad. Sci., U.S.A. 77, 5476–5479, Sep. 1980, Burton et al.
Biochemistry 14, 3188–1975, Suketa et al.
J. Org. Chem. 43, 3624, 1978; Rich et al.
Nature, 217, 456, 457, Feb. 1968, Kokubu.
J. Antibiotics 28, 1016–1018, 12/1975; Matsushita et al.
Biochem. Pharma. 23, 2776–2778, 1974; Lazar et al.
Biochem. Pharma. 21, 2941–2944, 1972; Miller et al.
Clinical Science 59, 7s–19s, 1980; Haber.
Biochemistry 14: 3892–3898, 1975, Burton et al.
Fed. Proc. Fed. Am. Soc. Exp. Biol. 38: 2768–2772, 1979; Haber & Burton.
Nature 299, 555 (1982), Hallett, Szelke.
Hypertension 4, Supp. 2, 59 (1981).
Acid Proteases, Structure, Func. & Biol. Plenum Press 1977, 141–157; Powers.
J. Antibiotic (Tokyo) 23: 259–262 1970; Umezawa et al.
Science 175: 656, 1971; Gross et al.
Circulation, 59, 60 Supp. II: 132 Oct. 1979); Tewksbury et al.
J. Exp. Med. 106, 439–453, 1957; Skeggs.
Biochem. Pharmacol. 22, 3217–3223, 1973; Kokubu et al.
Poulsen et al., Biochimica et Biophysica Acta, vol. 452, 1976, pp. 533–537.

*Primary Examiner*—Delbert R. Phillips
*Attorney, Agent, or Firm*—Richard A. Elder; Raymond M. Speer; Hesna J. Pfeiffer

[57] ABSTRACT

Renin inhibitory peptides of the formula

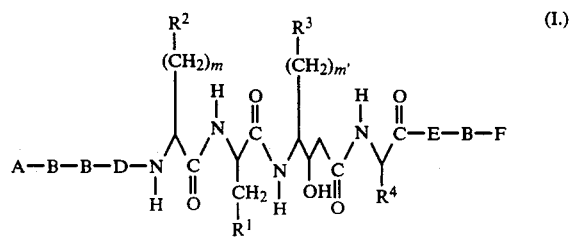

and analogs thereof inhibit renin and are useful for treating various forms of renin-associated hypertension and hyperaldosteronism.

4 Claims, No Drawings

RENIN INHIBITORS CONTAINING HOMOPHE[8]

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
| --- | --- |
| Renin antibody | probably $10^{-6}$ |
| Pepstatin | $10^{-6} - 10^{-7}$ |
| Phospholipids | $10^{-3}$ |
| Substrate analogs | |
| Tetrapeptides | $10^{-3}$ |
| Octa- to tridecapeptides | $10^{-5} - 10^{-6}$ |

Umezawa et al., in *J. Antibiot.* (Tokyo) 23: 259-262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

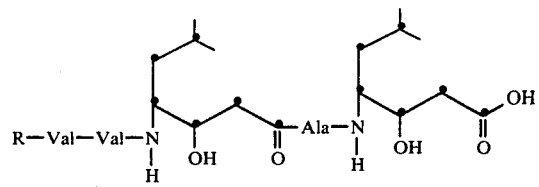

To date, many efforts have been made to prepare a specific renin inhibitor based on substrate analogy. Since the human renin substrate has only recently been elucidated (Tewksbury et al., *Circulation* 59, 60, Supp. II: 132, October 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533-537, 1976; and Skeggs, Jr. et al., *J. Exp. Med.* 106: 439-453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

```
    6    7    8    9   10   11   12   13
 —His—Pro—Phe—His—Leu—Leu—Val—Tyr—
```

Renin cleaves this substrate between Leu[10] and Leu[11].

Kokubu et al., *Biochem. Pharmacol.* 22: 3217-3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892-3898, 1975, and Poulsen et al., *Biochemistry* 12: 3877-3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768-2773, 1979.

More recently, Hallett, Szelke, and Jones, in work described in European Patent Publication No. 45,665 *Nature*, 299, 555 (1982), and *Hypertension*, 4, Supp. 2, 59

(1981), have replaced the Leu-Leu site of renin cleavage by isosteric substitution, and obtained compounds with excellent potency.

Powers et al., in *Acid Proteases, Structure, Function and Biology*, Plenum Press, 1977, 141–157 have suggested that in pepstatin, statine occupies the space of the two amino acids on either side of the cleavage site of a pepsin substrate, and Tang et al., in *Trends in Biochem. Sci.*, 1: 205–208 (1976) and *J. Biol. Chem.*, 251: 7088–94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Veber and Rich, in U.S. Pat. No. 4,384,994 and published European patent application No. 0,077,029; Evans and Rittle, in U.S. Pat. No. 4,397,786; Veber and Boger, in published European patent application No. 0,077,028; Boger et al, *Nature*, 303: 81–84 (1983); have all described renin inhibitory peptides containing statine. However, none of these references describe or suggest the HomoPhe[8] improvement of the present invention and the significant increase in renin inhibitory activity obtainable therewith.

For other articles describing previous efforts to devise renin inhibitors, see Marshall, *Federation Proc.* 35: 2494–2501, 1976; Burton et al., *Proc. Natl. Acad. Sci. USA* 77: 5476–5479, September 1980; Suketa et al., *Biochemistry* 14: 3188, 1975; Swales, *Pharmac. Ther.* 7: 173–201, 1979; Kokubu et al., *Nature* 217: 456–457, Feb. 3, 1968; Matsushita et al., *J. Antibiotics* 28: 1016–1018, December 1975; Lazar et al., *Biochem. Pharma.* 23: 2776–2778, 1974; Miller et al., *Biochem. Pharma.* 21: 2941–2944, 1972; Haber, *Clinical Science* 59: 7s–19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

$$\text{(I.)}$$

$$A-B-B-D-N\begin{matrix}R^2\\|\\(CH_2)_m\\|\\H\\|\\\end{matrix} \begin{matrix}O\\||\\C\\||\\O\end{matrix} \begin{matrix}H\\|\\N\\|\\CH_2\\|\\R^1\end{matrix} \begin{matrix}R^3\\|\\(CH_2)_{m'}\\|\\C\\|\\OH\\|\\H\end{matrix} \begin{matrix}H\\|\\N\\|\\C-E-B-F\\||\\O\end{matrix} \begin{matrix}\\R^4\end{matrix}$$

wherein:

A is hydrogen;

$$R^3-O-CH_2-\overset{O}{\underset{\|}{C}}-; \; R^3-CH_2-O-\overset{O}{\underset{\|}{C}};$$

$$R^3-O-\overset{O}{\underset{\|}{C}}; \text{ or } R^3-(CH_2)_n-\overset{O}{\underset{\|}{C}}-,$$

where n is 0 to 5 and R[3] has the same meaning as set out further below, and may additionally be hydrogen;

B is absent; glycyl; sarcosyl; or $$-N\begin{matrix}R^1\\|\\CH_2\\|\\H\end{matrix}\overset{}{\underset{}{C}}-\overset{}{\underset{O}{\|}},$$

where R[1] has the same meaning as set out further below;

D is absent; or

[structure with Z, N ring, and C=O]

where Z is $-(CH_2)_p-$ and p is 1 or 2; or $-S-$;

E is (1) $-Y-(CH_2)_q-R^6$ where

Y is $-NH-$ or $-O-$;

q is 0 to 5; and

R[6] is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di- $C_{1-4}$alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

$$-Y-(CH_2)_r-\overset{(CH_2)_{r''}-R^6}{\underset{\underset{OH_{r'}}{|}}{\overset{|}{CH}}}\overset{}{\underset{CH-(CH_2)_{r'''}-R_a^6}{|}} \quad (2)$$

where

Y is as defined above;

r is 0 or 1;

r' is 0 or 1;

r'' is 1 to 4;

r''' is 1 to 4; and

R[6] and R$_a$[6] may be the same or different and have the same meaning as

R[6] above and R$_a$[6] may additionally be $$\overset{O}{\underset{\|}{C}}\diagdown\underset{\underset{H}{|}}{N}\diagup^{R^7} \text{ or } \overset{O}{\underset{\|}{C}}\diagdown OR^7,$$

where R[7] is hydrogen or $C_{1-3}$alkyl;

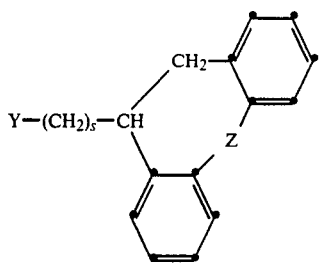

where
Y is as defined above;
s is 0 or 1; and
Z is

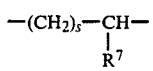 (a)

where
s is 0 or 1; and
R⁷ is as defined above; or

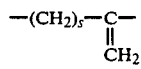 (b)

where
s is 0 or 1;

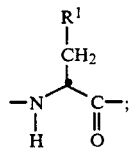 (4)

(5) absent;

F is absent; OR; NHR; or N(R)₂, where R may be the same or different and is hydrogen or $C_{1-4}$alkyl;

$R^1$ is hydrogen; $C_{1-4}$alkyl; hydroxy $C_{1-4}$alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$alkyl; quanidyl $C_{2-3}$alkyl; or methylthiomethyl;

$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^3$ is $C_{3-6}$alkyl; $C_{3-7}$cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

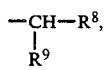

where $R^8$ is hydrogen; $C_{1-4}$alkyl; hydroxy; or $C_{3-7}$cycloalkyl; and $R^9$ is hydrogen; $C_{1-4}$alkyl; aryl; aryl $C_{1-4}$alkyl; aryl$C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

m is 2 to 4;
m′ is 1 to 4; and wherein all of the asymmetric carbon atoms have an S configuration, except for those in the A, B, D, and E substituents, which may have an S or R configuration; and a pharmaceutically acceptable salt thereof.

While both the S and R chiralities for asymmetric carbon atoms in the A, B, D, and E substituents are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl$C_{1-4}$alkyl.

The novel renin inhibitory peptides of the present invention may also be described in terms of common amino acid components and closely related analogs thereof, in accordance with the following formula:

$$A\text{—}B\text{—}B\text{—}D\text{—}G\text{—}H\text{—}Sta\text{—}I\text{—}E\text{—}B\text{—}F. \qquad (II)$$

The A, B, D, E and F components correspond to the same portions of Formula I.

In Formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

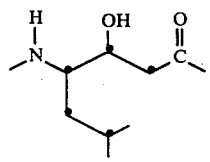 (III)

As shown in Formula III above, the delta-substituent in naturally-occurring statine is isopropyl, or a leucine sidechain, essentially. As shown in Formula I by the $R^3$ substituents, the isopropyl group may be replaced by higher alkyl groups up to six carbon atoms, cycloalkyl groups containing from three to seven carbon atoms, aryl, and $C_{3-7}$cycloalkyl or aryl substituted with up to three members selected from the group consisting of $C_{1-4}$alkyl, trifluoromethyl, hydroxy, $C_{1-4}$alkoxy, fluoro, chloro, bromo, and iodo. A phenyl substituent and a cyclohexyl substituent are especially preferred. These modifications of the naturally-occurring statine structure are in accordance with the hydrophobicity considered necessary to maintain the inhibitory activity of the total peptide.

The remaining common amino acid components of Formula II are as follows:

A has the same meaning as above in Formula I;
B is Ala, Leu, Ser, Thr, Phe, Tyr, Trp, His, Lys, Orn, Arg, or Met;
D is Pro;
G is HomoPhe, HomoTyr, or HomoTrp;
H is the same as B;
I is Gly, Ala, Val, Leu, Ile, Ser, Thr, Phe, Tyr, or Trp;
E has the same meaning as above in Formula I;
B is as defined above; and
F has the same meaning as above in Formula I.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of naturally-occurring statine represented by the definitions of the $R^3$ substituent in Formula I, represent preferred peptides of the present invention.

Preferred inhibitory peptides of the present invention are the following:

| | |
|---|---|
| IVA[1] | —His—Pro—Hph[2]—His—Sta—Leu—Phe—NH$_2$ |
| IVA | —His—Pro—Hph—His—ACHPA[3]—Leu—Phe—NH$_2$ |
| IVA | —His—Pro—Hph—His—Sta—Ile—His—NH$_2$ |

IVA

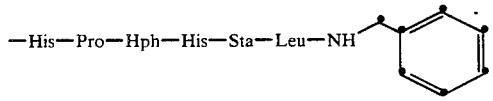

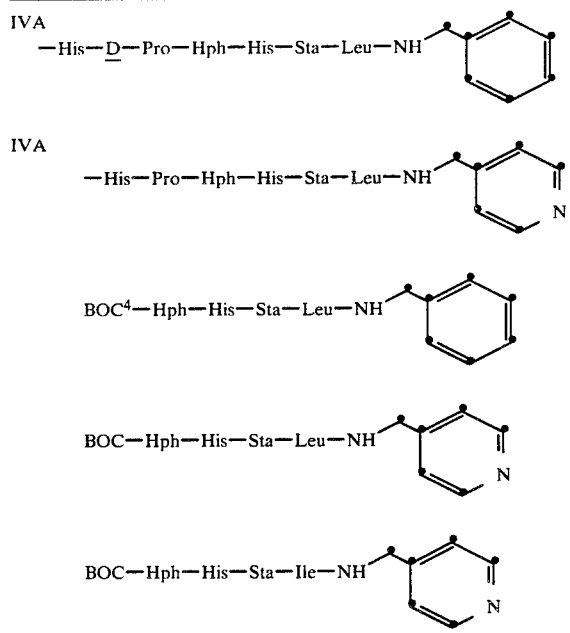

[1] IVA = Iso-valeryl.
[2] Hph = L—Homophenylalanine.
[3] ACHPA = (3S, 4S)—4-Amino-5-cyclohexyl-3-hydroxy-pentanoic acid.
[4] BOC = Tert-butyloxycarbonyl The inhibitory peptides of the present invention may be better appreciated in terms of substrate analogy from the following illustration of Formula I alongside the octapeptide sequence of a portion of the pig renin substrate, which renin cleaves between Leu[10] and Leu[11].

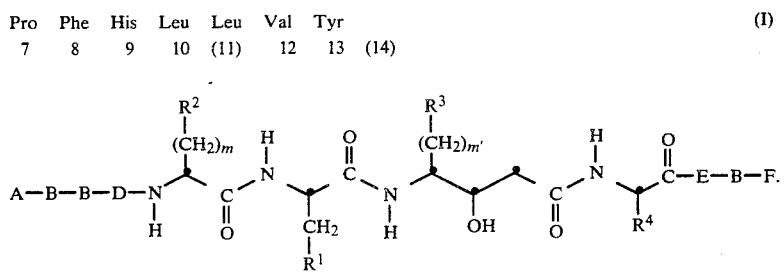

As can be seen, a unique aspect and essential feature of the present invention is the substitution of the single statine or derivative amino acid component for the double amino acid sequence: Leu[10]-Leu[11] in the endogenous pig renin substrate. It is believed that substitution of statine for both luecine amino acids rather than just one leucine results in an improved substrate analogy due to the greater linear extent of statine as compared to a single leucine component. Thus, statine more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu[10] and Val[11]:

Statine

| Pro | Phe | His | Leu | Val | Ile | His |     | (I) |
|-----|-----|-----|-----|-----|-----|-----|-----|-----|
| 7   | 8   | 9   | 10  | (11)| 12  | 13  | (14)|     |

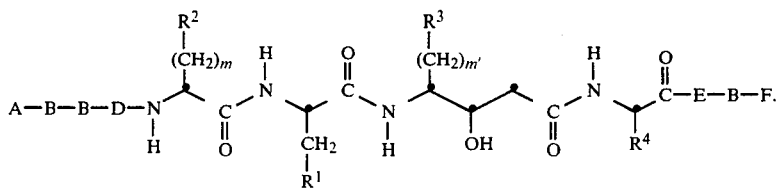

As can be seen, a unique aspect and essential feature of the present invention is the substitution of the single statine or derivative amino acid component for the double amino acid sequence: $Leu^{10}$—$Val^{11}$ in the endogenous human renin substrate. It is believed that substitution of statine for both the leucine and valine amino acids rather than just the leucine results in an improved substrate analogy due to the greater linear extent of statine as compared to a single leucine component. Thus, statine more closely approximates Leu-Val in linear extent, and thereby provides a better "fit" to the human renin enzyme.

In the endogenous substrate it is also preferred to substitute Leu for $Val^{12}$ and Phe for $Tyr^{13}$ in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are waer, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

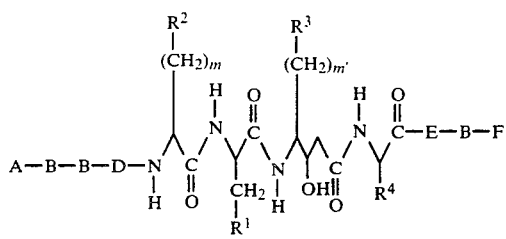

(I.)

wherein A, B, D, R², R¹, R³, R⁴, E, and F have the same meaning as recited further above for Formula I; wherein all of the asymmetric carbon atoms have an S configuration, except for those in the A, B, D, and E substituents, which may have an S or R configuration; and a pharmaceutically acceptable salt thereof.

Also, in accordance with the present invention there is still further provided a method of treating renin-associated hypertension and hyper-aldosteronism, comprising administering to a patient in need of such treatment, a therapeutically effective amount of a peptide of the formula:

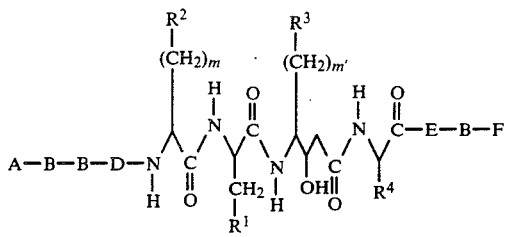

(I.)

wherein A, B, D, R², R¹, R³, R⁴, E, and F have the same meaning as recited further above for Formula I; wherein all of the asymmetric carbon atoms have an S configuration, except for those in the A, B, D, and E substituents, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral admininstration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described by Rich et. al., *J. Org. Chem.* 43: 3624 (1978).

A general method of preparation may be described in the following terms; wherein amino acids forming peptides of various lengths are sequentially assigned a Roman numeral for each peptide, rather than on the basis of a position in the overall peptide Formula I:

A method of preparing a peptide of formula I, said peptide being comprised of from four to nine amino acids identified as I through IX, amino acid (AA) I being at the C-terminus of said peptide, to which substituent F is attached, and amino acid (AA) IV through IX, depending upon the number of amino acids present, being at the N-terminus of said peptide, to which substituent A is attached, comprising the steps of:

(A) treating an ester of the C-terminus amino acid (AA I) with the next adjacent amino acid (AA II) of said peptide, the amino group of said amino acid being protected by a protecting group, in the presence of a condensing agent, whereby a dipeptide of the two amino acids (AA I and II) is formed;

(B) deprotecting the dipeptide formed in Step (A) by removing the protecting group from the amino group of AA II;

(C) repeating the procedures of Steps A and B successively to form a tetrapeptide to a nonapeptide of Formula I wherein A is hydrogen, F is hydroxy, and E is absent;

(D) optionally forming the $C_{1-4}$alkyl ester or amide of the tetrapeptide to nonapeptide of Step (C), to give the peptide of Formula I wherein F is other than hydroxy;

(E) treating the tetrapeptide to nonapeptide formed in Step (D) with a suitably substituted acid halide, anhydride, or other carbonyl activating group, to give the peptide of Formula I wherein A is other than hydrogen; and optionally (F) treating the peptide of Step (D) where B and F are absent, a tetra- to heptapeptide, with hydrazine to give the corresponding hydrazide, followed by treatment of said hydrazide with acidic nitrite to give the corresponding acyl azide, followed by treatment of said acyl azide with the appropriate amine compound to give the desired E substituent in the peptide of Formula I when B and F are absent; said method also comprising, where necessary, protection of sidechain substituents of the component amino acids AA I through AA IX, with deprotection being carried out as a final step; said method also comprising any combination of the steps set out above, whereby the amino acids I through IX and substituent A is assembled in any desired order to prepare the peptide of Formula I; said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide from said synthetic resin substrate: (a) by strong acid cleavage to give F=OH; (b) by transesterification with $C_{1-4}$ alkanol to give E=O-$C_{1-4}$alkyl; or (c) by ammonolysis with $NH_2R$; said removal steps also optionally being carried out as treatments where solid phase sequential synthesis is not carried out, to give the same F substituent endings; removal of side-chain protecting groups being accomplished either before or after removal of the peptide from said synthetic resin substrate; the steps of cyclization and formation of the A substituent in said method being accomplished at any time and in any order during preparation of peptides of different linear extent, after preparation of the minimal quadripeptide as recited above.

A preferred method involves preparation of the peptide of desired linear extent and desired A, E, and F substituents by solid phase sequential synthesis. An homologous amino acid is substituted in the solid phase step corresponding to addition of position-8. The preferred position-8 substitution is L-homophenylalanine, which is commercially available in chirally pure form. This $N^\alpha$-BOC-L-2-phenylethylalanine is incorporated during solid phase synthesis as the N-α-BOC derivative, as with other amino acids, and requires no special treatment. Preparation of other homologous amino acids for substitution at the 8-position, and as statine derivatives, may be carried out in a straightforward manner using known methods. For example, synthesis of BOC-DL-BisHomoPhe is accomplished in accordance with the procedure schematically represented below:

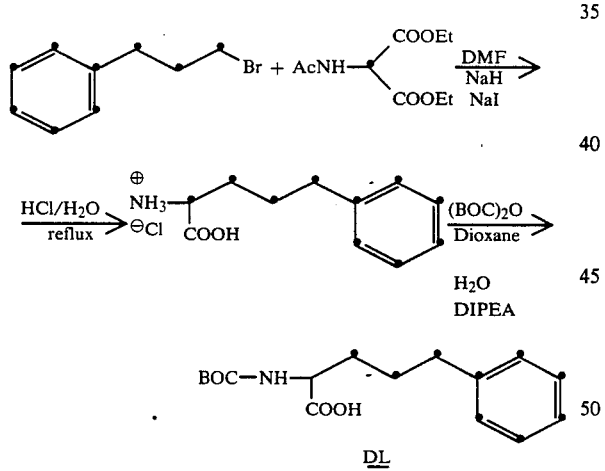

The phenyl analog of statine, (3S,4S)-4-amino-3-hydroxy-5-phenylpentanoic acid (AHPPA) can be prepared in accordance with the procedure described by Rich et al., *J. Med. Chem.* 23: 27-33 (1980).

Other analogs of statine may be prepared in a straightforward manner. For example, the cyclohexylalanine analog of statine, (3S, 4S)-4-amino-5-cyclohexyl-3-hydroxypentanoic acid (ACHPA) can be prepared by catalytic hydrogenation (using $H_2$/Rh on alumina, or other suitable catalyst) of the BOC-AHPPA, prepared as described in the paragraph immediately above. Alternatively, this and similar statine analogs can be prepared in accordance with the procedure described for statine, where the BOC-Leu starting material is replaced with the amino acid containing the desired side chain. Thus, BOC-ACHPA can also be prepared starting from BOC-L-cyclohexylalanine, itself prepared, for example, by catalytic reduction of BOC-Phe, in the same manner as described for BOC-AHPPA.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | |
|---|---|
| | Amino Acid |
| AHPPA | (3S,4S)—4-amino-3-hydroxy-5-phenylpentanoic acid |
| ACHPA | (3S,4S)—4-amino-5-cyclohexyl-3-hydroxypentanoic acid |
| Ala | L-alanine |
| Arg | L-arginine |
| DAB | 2-S—amino-4-aminobutyric acid |
| Gly | L-glycine |
| His | D or L-histidine |
| HLys | homolysine, 2S—amino-6-amino-heptanoic acid |
| Ile | L-isoleucine |
| Leu | L-leucine |
| Lys | L-lysine |
| Met | L-methionine |
| Orn | L-ornithine |
| Phe | L-phenylalanine |
| Ser | L-serine |
| Sar | L-sarcosine (N—methylglycine) |
| Sta | (3S,4S)—statine |
| Thr | L-threonine |
| Trp | L-tryptophan |
| Tyr | L-tyrosine |
| Val | L-valine |
| | Protecting Groups |
| BOC | tert-butyloxycarbonyl |
| CBZ | benzyloxycarbonyl |
| 2-Cl—CBZ | 2-chlorobenzyloxycarbonyl |
| IBU | iso-butyryl |
| IVA | iso-valeryl |
| DNP | dinitrophenyl |
| OMe | methyl ester |
| | Activating Groups |
| HBT | 1-hydroxybenzotriazole |
| | Condensing Agents |
| DCCI | dicyclohexylcarbodiimide |
| DPPA | diphenylphosphorylazide |
| | Reagents |
| TEA | triethylamine |
| TFA | trifluoroacetic acid |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20-70 microns in diameter) of a synthetic resin prepared by copolymerization of styrene with 1-2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl(carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which however, are not intended to be any limitation of the present invention.

EXAMPLE 1

$N^\alpha$-Isovaleryl-L-Histidyl-L-Prolyl-L-Homophenylalanyl-L-Histidyl-(3S,4S)-Statyl-L-Leucyl-L-Phenylalanyl Amide The title peptide was prepared by standard solid phase and solution methods as described below. The use of DL-homophenylalanine in the synthesis led to the expected two diastereomers, which were separated as described and identified by $^1$H NMR comparisons with the analogous phenylalanine-containing compounds. In general, the use of readily available L-homophenylalanine is to be preferred since this avoids the need for this separation step.

Step A:
$N^\alpha$-Isovaleryl-L-Histidyl-L-Prolyl-L-Homophenylalanyl-L-Histidyl-(3S,4S)-Statyl-L-Leucyl-L-PHenylalanyl-O-Resin The title peptide resin was prepared by standard solid phase methodology, as described in Erickson & Merrifield, Proteins, 3rd. ed., 2, 257-527, 1971, using a Beckman 990B peptide synthesizer to carry out the operations according to the attached programs. The starting polymer was BOC-Phe esterified to 2% cross-linked polystyrene-divinylbenzene (2 mmol, 1.67 g). The $N^\alpha$-BOC derivatives of His-(DNP), Pro and Leu were coupled using dicyclohexylcarbodiimide with an equivalent of the additive 1-hydroxybenzotriazole hydrate. The Sta was prepared in accordance with Rich, et al., J. Org. Chem. 43 3624, 1978. The BOC-group was removed with 40% trifluoroacetic acid. A coupling of 30 minutes followed by a recoupling of 60 minutes (2.5 equivalents each time of BOC-amino acid were used for each amino acid except Sta and DL-Homophenylalanine). In order to conserve the amounts of the latter two, an initial coupling of 1.25 equivalents of BOC-amino acid (in 1:1 $CH_2Cl_2$/DMF), with DCC and 1 equivalent of $HBT.H_2O$) for 18 hours was followed by steps 1–3 of the recouple program 2 and an additional coupling of 18 hours using the original (saved) coupling solution. This effected 99% complete reaction of the residues, preserving their supply. The N-terminal isovaleryl group was coupled for 30 minutes as a symmetrical anhydride generated in situ from 5.0 equivalents of isovaleric acid and 2.5 equivalents of DCC. This was followed by a recoupling also using the symmetrical anhydride. The DNP-protecting group on His was removed in the final program using two 25-minute treatments with 10% thiophenol in DMF. The finished resin was dried in vacuo.

Step B:
$N^\alpha$-Isovaleryl-L-Histidyl-L-Prolyl-L-Homophenylalanyl-L-Histidyl-(3S,4S)-Statyl-L-Leucyl-L-Phenylalanyl Amide One half of the completed resin (1 mmole, nominally) was suspended in a pressure bottle in 25 ml dry MeOH and saturated with $NH_3$ at $-50°$ C. or until the volume doubled to 50 ml. To this suspension was added 0.15 g ammonium acetate and the bottle was closed and stirred at room temperature for 2 days. The bottle was vented and the resin residue filtered off, washing it with MeOH and $CH_2Cl_2$. The combined filtrates were evaporated to 1.74 g of an orange residue. This was dissolved in 200 ml ethyl acetate and washed with 100 ml water. The organic layer was then washed with 50 ml 5% citric acid followed by the additional 25 ml washes. These three acidic washes were combined and neutralized with solid $K_2CO_3$, precipitating a yellow gum material. The now basic solution was extracted with $3 \times 100$ ml $CH_2CL_2$ plus 5 ml MeOH, which dissolved the gum also. These $CH_2Cl_2$ layers were combined, washed with water, dried over $Na_2SO_4$, filtered, and evaporated to give 0.95 g crude amide. On TLC chromatography, this material was seen to be two spots of equal intensity at $R_f$'s 0.37 and 0.26, 80:20:2:1, chloroform:methanol:water:acetic acid, somers A and B respectively.

Step C:
N$^\alpha$-Isovaleryl-L-Histidyl-L-Prolyl-L-Homophenylalanyl-L-Histidyl-(3S,4S)-Statyl-L-Leucyl-L-Phenylalanyl Amide The crude mixture in Step B containing the two diastereomers due to D and L-homophenylalanine was separated by colum chromatography on silica gel using a solvent of 100:20:2:1, chloroform:methanol:water:acetic acid, to give, after precipitation from CH$_2$Cl$_2$/ether, 145 mg of upper spot isomer A and a similar quantity of lower spot isomer B. Isomer A proved to be the L-homophenylanyl-containing compound by comparison of its 360 MHz $^1$H NMR spectrum with that of the similar compound containing L-phenylalanine, synthesized unambiguously from pure L-Phe. HPLC: 88% pure. TLC: 90% pure. 360 MHz $^1$H NMR consistent with structure. Elemental analysis consistent with trihydrated salt. Amino acid analysis: His$_{1.99}$ Pro$_{1.04}$ Sta$_{0.96}$ Leu$_{1.01}$ Phe$_{1.02}$ NH$_{30.99}$ HPhe$_{11.0}$.

The isomer B was similarly characterized as the D-HomoPhe analog. The D-diastereomer is at least 100-1000 times less active than the L for renin inhibition.

EXAMPLE 2

N$^\alpha$-Isovaleryl-L-Histidyl-L-Prolyl-L-Bishomophenylalanyl-L-Histidyl-(3S,4S)-Statyl-L-Leucyl-L-Phenylalanyl Amide The compound was prepared as described in Example 1, except BOC-DL-Bishomophenylalanine was used in the synthesis. This amino acid was prepared by standard methods according to the scheme described further above.

The L-isomer was separated and identified as for Example 1 and characterized: HPLC: 92%. TLC: 90%. Elemental analysis: consistent with 2.5 hydrate salt. 360 MHz $^1$H NMR: consistent with structure. Amino Acid analysis: His$_{2.00}$ Pro$_{1.00}$ BHP$_{n.d}$ Sta 1.00 Leu$_{1.00}$ Phe$_{1.01}$ NH$_{3n.d}$.

| SCHEDULE OF STEPS FOR 2 MMOL RUN ||||
| Step | Solvent/Reagent | Vol. (ml) | Mix time (min) |
| --- | --- | --- | --- |
| | Coupling Program 1 | | |
| 1 | CH$_2$Cl$_2$ | 6 × 20 | 2 |
| 2 | 40% TFA in CH$_2$Cl$_2$ | 1 × 20 | 2 |
| 3 | 40% TFA in CH$_2$Cl$_2$ | 1 × 20 | 25 |
| 4 | CH$_2$Cl$_2$ | 3 × 20 | 2 |
| 5 | 10% TEA in CH$_2$Cl$_2$ | 2 × 20 | 5 |
| 6 | CH$_2$Cl$_2$ | 3 × 20 | 2 |
| 7 | BOC—amino acid, HBT in 1:1 DMF/CH$_2$Cl$_2$ | 15 | 5 |
| 8 | 1.0 M DCCI in CH$_2$Cl$_2$ | 5 | 30 |
| 9 | DMF | 1 × 20 | 2 |
| 10 | MeOH | 2 × 20 | 2 |
| 11 | CH$_2$Cl$_2$ | 1 × 20 | 2 |
| | Re-Couple Program 2 | | |
| 1 | CH$_2$Cl$_2$ | 1 × 20 | 2 |
| 2 | 10% TFA in CH$_2$Cl$_2$ | 2 × 20 | 5 |
| 3 | CH$_2$Cl$_2$ | 3 × 20 | 2 |
| 4 | BOC—amino acid, HBT in 1:1 DMF/CH$_2$Cl$_2$ | 15 | 5 |
| 5 | 1.0 M DCCI in CH$_2$Cl$_2$ | 5 | 60 |
| 6 | DMF | 1 × 20 | 2 |
| 7 | MeOH | 2 × 20 | 2 |
| 8 | CH$_2$Cl$_2$ | 5 × 20 | 2 |
| | Program 3 (DNP removal) | | |
| 1 | CH$_2$Cl$_2$ | 1 × 20 | 2 |
| 2 | DMF | 2 × 20 | 2 |
| 3 | 10% phenylthiol in DMF | 1 × 20 | 25 |
| 4 | DMF | 1 × 20 | 2 |
| 5 | 10% TEA in CH$_2$Cl$_2$ | 1 × 20 | 2 |
| 6 | DMF | 2 × 20 | 2 |
| 7 | 10% phenylthiol in DMF | 1 × 20 | 25 |
| 8 | DMF | 3 × 20 | 2 |
| 9 | MeOH | 2 × 20 | 2 |
| 10 | CH$_2$Cl$_2$ | 2 × 20 | 2 |
| 11 | MeOH | 2 × 20 | 2 |
| 12 | CH$_2$Cl$_2$ | 2 × 20 | 2 |
| 13 | MeOH | 2 × 20 | 2 |

EXAMPLES 3–5

Following the standard solid phase methodology described above in Examples 1 and 2, additional inhibitory peptides of the present invention were prepared. The peptides prepared are set out in the following table. Satisfactory amino acid analyses were obtained by Spinco method for each listed peptide. In each of these cases, commercially available L-Homophenylalanine was converted to its BOC-derivative using ditertbutyldicarbonate and diisopropylethylamine in dioxane/water. The use of this chirally pure material obviated the separation of diastereomers as in Example 1.

| Example No. | Peptide |
| --- | --- |
| 3 | BocHPhe—His—ACHPA—Leu—OCH$_3$ |
| 4 | BocHPhe—His—ACHPA—Leu—NH$_2$ |
| 5 | BocHPhe—His—ACHPA—Leu—Phe—OCH$_3$ |

For the peptides prepared above, various analytical methods were carried out to verify the structure of the peptide products. The following table indicates which methods were employed and summarizes the results where practicable.

| Example No. | TLC[1] (No. of systems) | Analytical Method ||||
| --- | --- | --- | --- | --- | --- |
| | | HPLC[2] | AA[3] | EA[4] | NMR[5] |
| 3 | 95+% | 94% | X | X | X |
| 4 | 95% | 91.5% | X | X | X |
| 5 | 95+% | 99% | X | X | X |

[1]TLC = thin layer chromatography on silica gel; visualization by reagents which tend to detect peptides; % refers to estimated purity.
[2]HPLC = high pressure liquid chromatography; detection by ultraviolet absorption at 240 nm or 210 nm; chromatography is reverse phase, values should be 1.00 ± 0.03.
[3]AA = amino acid analysis; peptides are hydrolyzed to their component amino acids, which are then quantitatively measured; values should be 1.00 ± 0.03.
[4]EA = elemental analysis
[5]NMR = nuclear magnetic resonance spectroscopy at 360 MHz for protons; X = spectrum consistent with structure; = not performed.

EXAMPLE 6

Renin Inhibition

Assays were carried out in order to determine the inhibitory potency of the peptides of the present invention. One assay measured the inhibition of hog kidney renin, and was in accordance with the procedure described in Rich et al., *J. Med. Chem.* 23: 27, 1980, except that a pH of 7.3 was used. Another assay measured the inhibition of human kidney renin purified as described in Bangham, D. R., Robertson, I., Robinson, J. I. S., Robinson, C. J., and Tree, M., *Clinical Science and Molecular Medicine*, 48 (Supp. 2): 136s–159s (1975), and further purified by affinity chromatography on pepstatin-aminohexyl-Sepharase as described in Poe, M., Wu., J. K., Florance, J. R., Radkey, J. A., Bennett, C. D., and Hoogsteen, K., J. Biol. Chem. 258: 2209–2216 (1983). The assay was also in accordance with Poe et al. cited above. Further assays measured human plasma renin and dog plasma renin in accordance with procedures described in Boger et al, Nature, 303: 81–84 (1983).

Results expressed as $K_I$ values refer to the dissociation constant of the inhibited enzyme-inhibitor complex. This $K_I$ value was obtained as described above. Pepstatin was used as an active control. The results are set out in the table below.

| Peptide | Hog Kidney I50 (M) | Human Kidney KI (M) | Human Plasma I50 (M) | Dog Plasma I50 (M) |
|---|---|---|---|---|
| IVA—His—Pro—HomoPhe—His—Sta—Leu—Phe—NH$_2$ | $1.9 \times 10^{-8}$ | $3.3 \times 10^{-10}$ | $1.4 \times 10^{-10}$ | $4.5 \times 10^{-9}$ |
| IVA—His—Pro—BisHomoPhe—His—Sta—Leu—Phe—NH$_2$ | $1.3 \times 10^{-7}$ | $9.0 \times 10^{-8}$ | $3.1 \times 0^{-8}$ | $3.2 \times 10^{-7}$ |
| BOC—HomoPhe—His—ACHPA—Leu—OCH$_3$ | — | $9.8 \times 10^{-10}$ | — | — |
| BOC—HomoPhe—His—ACHPA—Leu—NH$_2$ | — | $1.17 \times 10^{-9}$ | $3.9 \times 10^{-9}$ | $1.0 \times 10^{-7}$ |
| BOC—HomoPhe—His—ACHPA—Leu—Phe—OCH$_3$ | — | $3.9 \times 10^{-10}$ | $4.0 \times 10^{-9}$ | $1.6 \times 10^{-8}$ |

What is claimed is:

1. A peptide of the formula: (I.)

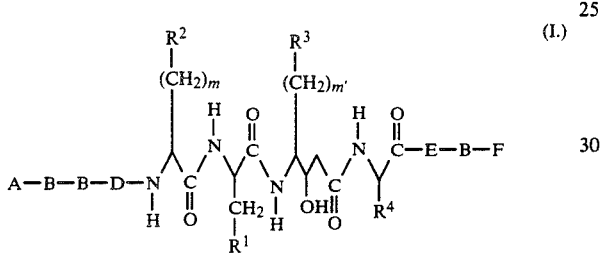

wherein:

A is hydrogen;

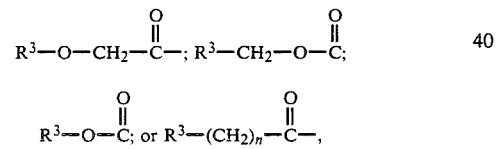

where n is 0 to 5 and $R^3$ has the same meaning as set out further below, and may additionally be hydrogen;

B is absent; glycyl; sarcosyl; or

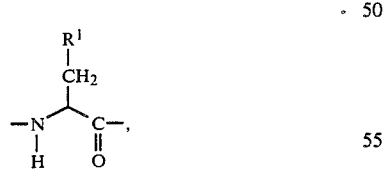

where $R^1$ has the same meaning as set out further below;

D is absent; or

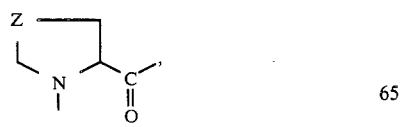

where Z is —(CH$_2$)$_p$— and p is 1 or 2; or —S—;

E is (1) —Y—(CH$_2$)$_q$—R$^6$ where

Y is —NH— or —O—;

q is 0 to 5; and R$^6$ is hydrogen; hydroxy; C$_{1-4}$alkyl; C$_{3-7}$cycloalkyl; aryl; aryl substituted with up to five members independently selected from the group consisting of C$_{1-6}$alkyl, trifluoromethyl, hydroxy, C$_{1-4}$alkoxy, amino, mono- or di-C$_{1-4}$ alkylamino, and halo; amino; mono-, di-, or tri-C$_{1-4}$alkylamino; guanidyl; heterocyclic; or heterocyclic substituted with up to five members independently selected from the group consisting of C$_{1-6}$alkyl, hydroxy, trifluoromethyl, C$_{1-4}$alkoxy, halo, aryl, aryl C$_{1-4}$alkyl, amino, and mono- or di-C$_{1-4}$alkylamino;

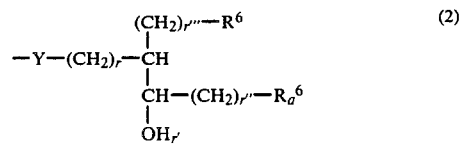

where

Y is as defined above;

r is 0 or 1;

r' is 0 or 1;

r'' is 1 to 4; and r''' is 1 to 4; and

R$^6$ and R$_a^6$ may be the same or different and have the same meaning as R$^6$ above and R$_a^6$ may additionally be

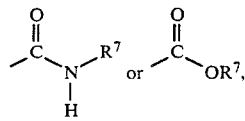

where R$^7$ is hydrogen or C$_{1-3}$alkyl;

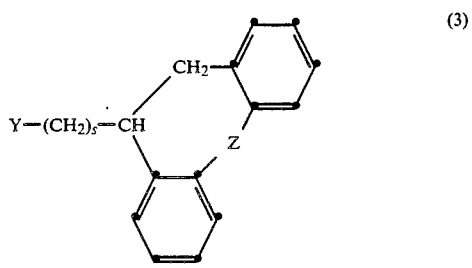

where

Y is as defined above;

s is 0 or 1; and

Z is

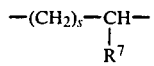 (a)

where
s is 0 or 1; and
R⁷ is as defined above; or

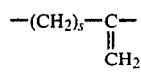 (b)

where
s is 0 or 1;

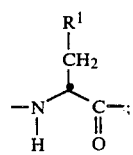 (4)

(5) absent;

F is absent; OR; NHR; or N(R)2, where R may be the same or different and is hydrogen or $C_{1-4}$alkyl;

$R^1$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$alkyl; quanidyl $C_{2-3}$alkyl; or methylthiomethyl;

$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

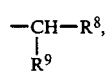

where $R^8$ is hydrogen; $C_{1-4}$alkyl; hydroxy; or $C_{3-7}$cycloalkyl; and $R^9$ is hydrogen; $C_{1-4}$alkyl; aryl; aryl $C_{1-4}$alkyl; aryl$C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

m is 2 to 4;
m' is 1 to 4; and
wherein all of the asymmetric carbon atoms have an S configuration, except for those in A, B, D, and E substituents, which may have an S or R configuration; and a pharmaceutically acceptable salt thereof.

2. A peptide according to claim 1 wherein the peptide is a member selected from the group consisting essentially of:

| | |
|---|---|
| IVA | —His—Pro—Hph—His—Sta—Leu—Phe—NH₂ |
| IVA | —His—Pro—Hph—His—ACHPA—Leu—Phe—NH₂ |
| IVA | —His—Pro—Hph—His—Sta—Ile—His—NH₂ |

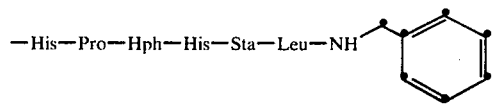

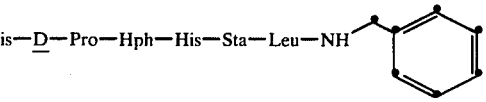

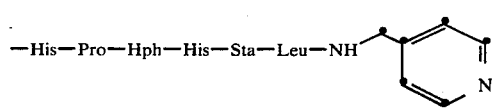

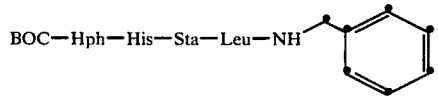

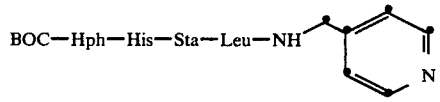

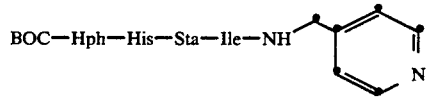

3. A pharmaceutical composition for treating renin-associated hypertension or renin-associated hyperaldosteronism, comprising a pharmaceutical carrier and a therapeutically effective amount of a peptide of the formula:

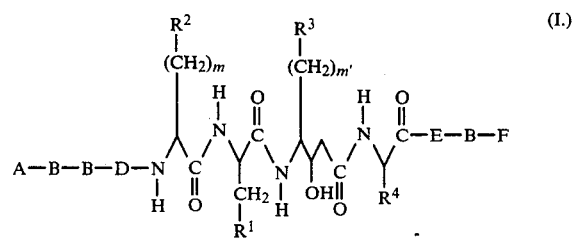 (I.)

wherein:

A is hydrogen;

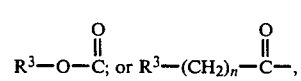

where n is 0 to 5 and $R^3$ has the same meaning as set out further below, and may additionally be hydrogen;

B is absent; glycyl; sarcosyl; or

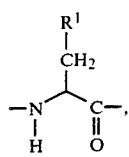

where R¹ has the same meaning as set out further below;

D is absent; or

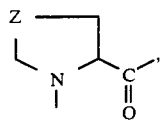

where Z is —(CH₂)$_p$—
and p is 1 or 2; or —S—;

E is (1) —Y—(CH₂)$_q$—R⁶ where

Y is —NH— or —O—;

q is 0 to 5; and

R⁶ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$ alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

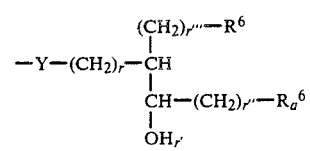
(2)

where

Y is as defined above;

r is 0 or 1;

r' is 0 or 1;

r" is 1 to 4;

r'" is 1 to 4; and

R⁶ and R$_a$⁶ may be the same or different and have the same meaning as R⁶ above and R$_a$⁶ may additionally be

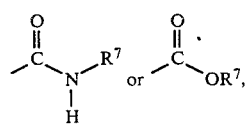

where R⁷ is hydrogen or $C_{1-3}$alkyl;

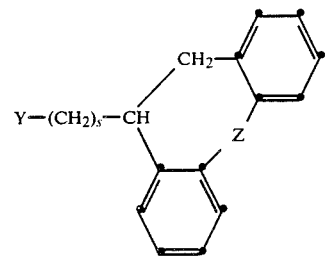
(3)

where

Y is as defined above;

s is 0 or 1; and

Z is

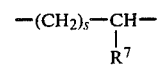
(a)

where s is 0 or 1; and

R⁷ is as defined above; or

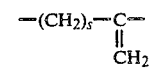
(b)

where s is 0 or 1;

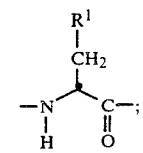
(4)

(5) absent;

F is absent; OR; NHR; or N(R)2, where R may be the same or different and is hydrogen or $C_{1-4}$alkyl;

R¹ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$alkyl; quanidyl $C_{2-3}$alkyl; or methylthiomethyl;

R² is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

R³ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

R⁴ is hydrogen; or

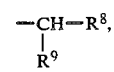

where R⁸ is hydrogen; $C_{1-4}$alkyl; hydroxy; or $C_{3-7}$cycloalkyl; and R⁹ is hydrogen; $C_{1-4}$alkyl; aryl; aryl $C_{1-4}$alkyl; aryl$C_{1-4}$alkyl or aryl where the aryl portion is substituted with up to three members selected from the group consisting of $C_{1-4}$alkyl, trifluoromethyl, hydroxy, C$_{1-4}$alkoxy, and halo; or indolyl;

m is 2 to 4;

m' is 1 to 4; and wherein all of the asymmetric carbon atoms have an S configuration, except for those in the A, B, D, and E substituents, which may have an S or R configuration; and a pharmaceutically acceptable salt thereof.

4. A composition according to claim 3 wherein the peptide is a member selected from the group consisting essentially of:

---

IVA —His—Pro—Hph—His—Sta—Leu—Phe—NH$_2$

IVA —His—Pro—Hph—His—ACHPA—Leu—Phe—NH$_2$

IVA —His—Pro—Hph—His—Sta—Ile—His—NH$_2$

IVA
—His—Pro—Hph—His—Sta—Leu—NH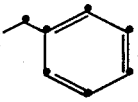

-continued

IVA
—His—D—Pro—Hph—His—Sta—Leu—NH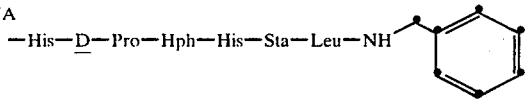

IVA
—His—Pro—Hph—His—Sta—Leu—NH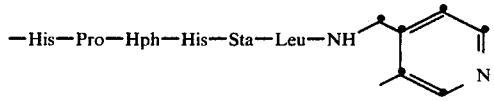

BOC—Hph—His—Sta—Leu—NH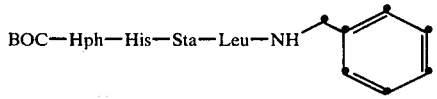

BOC—Hph—His—Sta—Leu—NH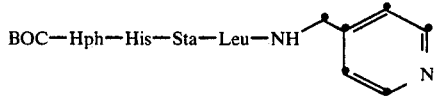

BOC—Hph—His—Sta—Ile—NH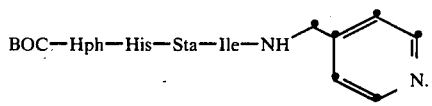

---

* * * * *